US009689338B2

(12) United States Patent
Uemura et al.

(10) Patent No.: US 9,689,338 B2
(45) Date of Patent: Jun. 27, 2017

(54) AIR-FUEL RATIO SENSOR CONTROL DEVICE

(71) Applicant: DENSO CORPORATION, Kariya, Aichi-pref. (JP)

(72) Inventors: Shinya Uemura, Obu (JP); Satoshi Ichikawa, Gamagori (JP)

(73) Assignee: DENSO CORPORATION, Kariya (JP)

( * ) Notice: Subject to any disclaimer, the term of this patent is extended or adjusted under 35 U.S.C. 154(b) by 206 days.

(21) Appl. No.: 14/680,155

(22) Filed: Apr. 7, 2015

(65) Prior Publication Data
US 2015/0323493 A1 Nov. 12, 2015

(30) Foreign Application Priority Data

May 7, 2014 (JP) .................. 2014-095985

(51) Int. Cl.
| *G01N 27/419* | (2006.01) |
| *G01N 27/417* | (2006.01) |
| *F02D 41/28* | (2006.01) |
| *F02D 41/14* | (2006.01) |
| *F02D 41/26* | (2006.01) |
| *G01N 27/406* | (2006.01) |

(52) U.S. Cl.
CPC ......... *F02D 41/28* (2013.01); *F02D 41/1454* (2013.01); *G01N 27/419* (2013.01); *G01N 27/4175* (2013.01); *F02D 41/266* (2013.01); *F02D 2041/281* (2013.01); *G01N 27/4065* (2013.01)

(58) Field of Classification Search
CPC .............. G01N 27/419; G01N 27/4175; F02D 41/1483; F02D 41/1461; F02D 41/1474; F02D 41/146; F02D 41/1455; F02D 41/1495
See application file for complete search history.

(56) References Cited

U.S. PATENT DOCUMENTS 4,765,880 A 8/1988 Hayakawa et al.
6,120,677 A 9/2000 Yamada et al.
(Continued)

FOREIGN PATENT DOCUMENTS

JP 11-174020 A 7/1999
JP 11-230931 A 8/1999
(Continued)

OTHER PUBLICATIONS

Information Offer Form issued Jan. 29, 2016 in the corresponding JP application No. 2014-095985 (with English translation).

*Primary Examiner* — Gurpreet Kaur
(74) *Attorney, Agent, or Firm* — Posz Law Group, PLC

(57) ABSTRACT

An air-fuel ratio sensor control device, connected with two-cell type air-fuel ratio sensor having electromotive force and oxygen pump cells with first to third two-cell terminals or a one-cell type air-fuel ratio sensor having a single cell with first and second one-cell terminals, includes: first to third connection terminals for connecting the one-cell or two-cell type air-fuel ratio sensor; a control circuit that is switchable between a two-cell circuit configuration for controlling the two-cell type air-fuel ratio sensor through the first to third connection terminals and a one-cell circuit configuration for controlling the one-cell type air-fuel ratio sensor through the first and second connection terminals; and a control unit that sets a circuit configuration of the control circuit to the one-cell or two-cell circuit configuration.

4 Claims, 12 Drawing Sheets

(56) References Cited

U.S. PATENT DOCUMENTS

| | | |
|---|---|---|
| 6,352,632 B1 | 3/2002 | Inagaki et al. |
| 2011/0199709 A1 | 8/2011 | Ieda |
| 2012/0266657 A1 | 10/2012 | Barnikow et al. |

FOREIGN PATENT DOCUMENTS

| | | |
|---|---|---|
| JP | 2003-287517 A | 10/2003 |
| JP | 2005-315757 A | 11/2005 |

FIG. 2

|  | IDLE MODE | 1-CELL MODE | 2-CELL MODE | LABEL RESIST MEAS MODE |
|---|---|---|---|---|
| SW1 | OFF | ON | OFF | OFF |
| SW2 | OFF | OFF | ON | OFF |
| SW3 | OFF | OFF | OFF | ON |
| SW4 | OFF | OFF | ON | OFF |
| SW5 | OFF | ON | OFF | OFF |
| SW6 | OFF | OFF | ON | ON |
| SW7 | OFF | OFF | ON/OFF CONT | OFF |
| SW8 | OFF | OFF | ON/OFF CONT | OFF |
| SW9 | OFF | OFF | OFF | ON |
| SW10 | OFF | ON | ON | OFF |
| SW11 | OFF | ON | ON | OFF |
| SW12 | OFF | OFF | ON | OFF |

AIR-FUEL RATIO SENSOR CONTROL DEVICE

CROSS REFERENCE TO RELATED APPLICATION

This application is based on Japanese Patent Application No. 2014-95985 filed on May 7, 2014, the disclosure of which is incorporated herein by reference.

TECHNICAL FIELD

The present disclosure relates to a control device for an air-fuel ratio sensor.

BACKGROUND

As the air-fuel ratio sensor, there is a two-cell type having an electromotive force cell and an oxygen pump cell which are oxygen concentration cells. In the air-fuel ratio sensor of the two-cell type, a pump current flowing in an oxygen pump cell is controlled so that an output voltage of the electromotive force cell reaches a target value, and the pump current is detected as a sensor current corresponding to an air-fuel ratio (for example, refer to Patent Document 1).

Also, as the air-fuel ratio sensor, there is a one-cell type having a single cell into which a current corresponding to the air-fuel ratio flows in a state where a voltage is applied thereto. In the air-fuel ratio sensor of the one-cell type, the current flowing in the cell is detected as the sensor current corresponding to the air-fuel ratio (for example, refer to Patent Document 2).

In each of the air-fuel ratio sensor of the one-cell type and the air-fuel ratio sensor of the two-cell type, to manufacture a control device having a dedicated hardware is disadvantageous to a reduction in the manufacturing cost of the control device since the variety of the control devices increases, and the number of manufacturing the respective control devices does not increase.

[Patent Document 1] JP-A-10-48180 (corresponding to U.S. Pat. No. 6,120,677)

[Patent Document 2] JP-A-11-230931

SUMMARY

It is an object of the present disclosure to provide an air-fuel ratio sensor control device that can be shared by the air-fuel ratio sensor of the one-cell type and the air-fuel ratio sensor of the two-cell type.

According to an aspect of the present disclosure, an air-fuel ratio sensor control device is connected with one of: a two-cell type air-fuel ratio sensor having an electromotive force cell and an oxygen pump cell, which are oxygen concentration cells in such a manner that a pump current flowing in the oxygen pump cell is controlled so that an output voltage of the electromotive force cell reaches a target value, and the pump current becomes a current corresponding to an air-fuel ratio; and a one-cell type air-fuel ratio sensor having a single cell, in which a current corresponding to the air-fuel ratio flows under a state where a voltage is applied to the single cell. The two-cell type air-fuel ratio sensor includes: a first two-cell terminal that is connected to one of a pair of electrodes in the oxygen pump cell; a second two-cell terminal that is connected to both of the other of the pair of electrodes in the oxygen pump cell and one of a pair of electrodes in the electromotive force cell; and a third two-cell terminal that is connected to the other of the pair of electrodes in the electromotive force cell, as terminals for controlling the air-fuel ratio sensor. The one-cell type air-fuel ratio sensor includes: a first one-cell terminal that is connected to one of a pair of electrodes in the single cell; and a second one-cell terminal that is connected to the other of the pair of electrodes in the single cell, as terminals for controlling the air-fuel ratio sensor. The air-fuel ratio sensor control device includes: a first connection terminal, a second connection terminal, and a third connection terminal, as terminals for connecting one of the two-cell type air-fuel ratio sensor and the one-cell type air-fuel ratio sensor; a control circuit that is switchable, by turning on and off at least one changeover switch, between a one-cell circuit configuration and a two-cell circuit configuration, the two-cell circuit configuration controlling the two-cell type air-fuel ratio sensor through the first, second, and third connection terminals, and the one-cell circuit configuration controlling the one-cell type air-fuel ratio sensor through the first and second connection terminals; and a control unit that sets a circuit configuration of the control circuit to one of the one-cell circuit configuration and the two-cell circuit configuration, by controlling the at least one changeover switch.

In the above air-fuel ratio sensor control device, the air-fuel ratio sensor control device can be shared by the air-fuel ratio sensor of the one-cell type, and the air-fuel ratio sensor of the two-cell type.

BRIEF DESCRIPTION OF THE DRAWINGS

The above and other objects, features and advantages of the present disclosure will become more apparent from the following detailed description made with reference to the accompanying drawings. In the drawings:

FIG. 2 is an illustrative view illustrating a state of switches in respective modes of a control circuit;

DETAILED DESCRIPTION

A description will be given of an air-fuel ratio sensor control device according to an embodiment of the invention. Incidentally, the air-fuel ratio sensor control device (hereinafter referred to as "ECU") according to this embodiment is used in a fuel injection control system for implementing an air-fuel ratio feedback control (control for regulating a fuel injection quantity to a target air-fuel ratio) of an internal combustion engine mounted in a vehicle.

Figure 1:
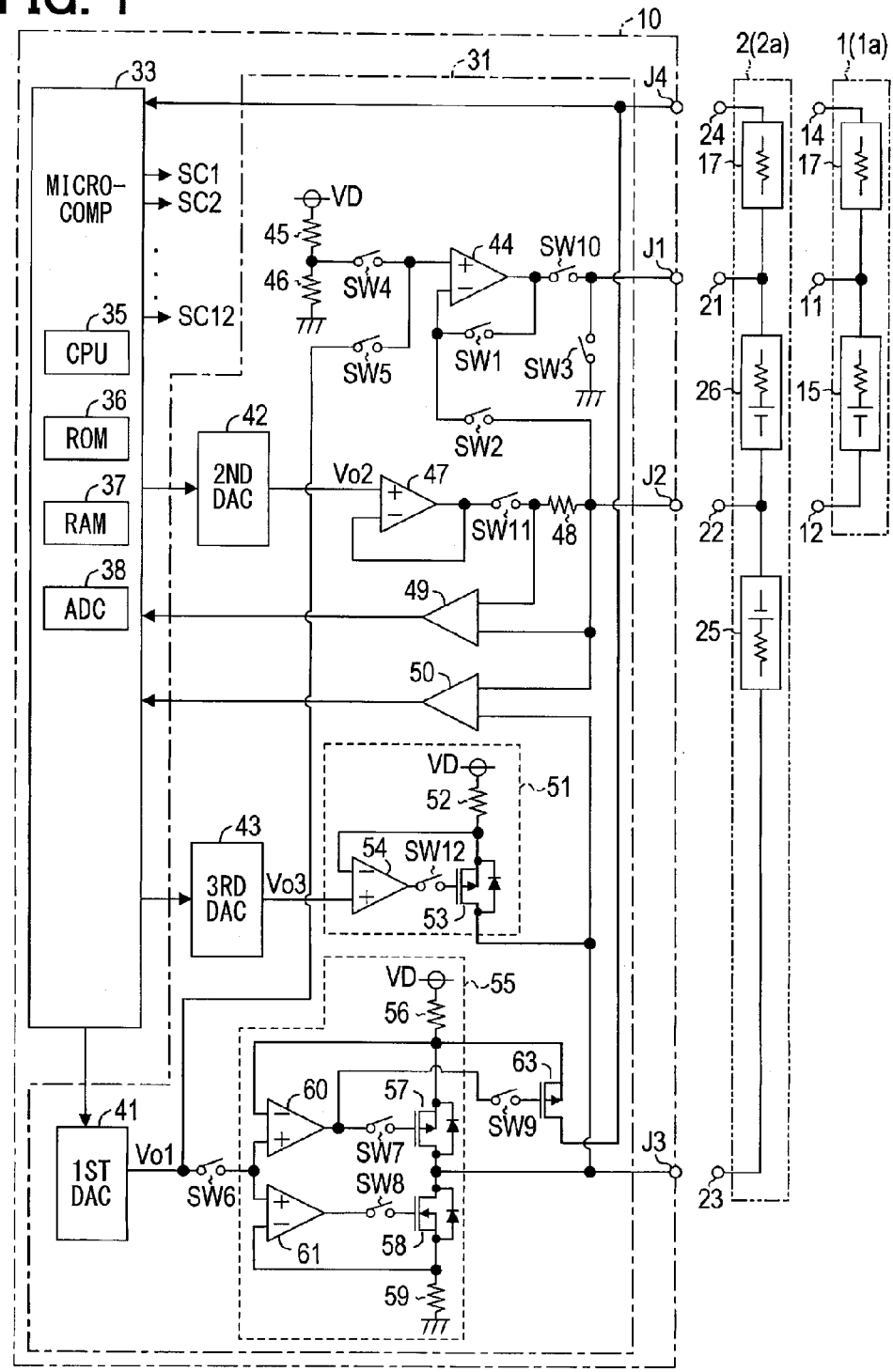
FIG. 1 is a configuration diagram illustrating an air-fuel ratio sensor control device according to an embodiment.

As illustrated in FIG. 1, an ECU 10 according to this embodiment is connected with any one of an air-fuel ratio sensor 1 of a one-cell type, and an air-fuel ratio sensor 2 of a two-cell type as an air-fuel ratio sensor.

The air-fuel ratio sensor (hereinafter referred to as "one-cell air-fuel ratio sensor") 1 of a one-cell type has a single cell 15 into which a current corresponding to an air-fuel ratio flows in a state where a voltage is applied. For that reason, in the one-cell air-fuel ratio sensor 1, a current flowing in the cell 15 is detected as a sensor current corresponding to an air-fuel ratio. The one-cell air-fuel ratio sensor 1 is an air-fuel ratio sensor of a limiting current type.

The cell 15 includes a solid electrolyte body made of, for example, zirconia, and a pair of electrodes provided on both surfaces (an atmospheric side and an exhaust side) of the solid electrolyte body. The one-cell air-fuel ratio sensor 1 includes, as terminals for controlling the air-fuel ratio sensor 1, a terminal 11 connected to one of the pair of electrodes provided in the cell 15, and a terminal 12 connected to the other of the pair of electrodes provided in the cell 15.

On the other hand, the air-fuel ratio sensor (hereinafter referred to as "two-cell air-fuel ratio sensor") 2 of the two-cell type includes an electromotive force cell 25 and an oxygen pump cell 26 which are oxygen concentration cells. In the two-cell air-fuel ratio sensor 2, a pump current flowing into the oxygen pump cell 26 is controlled so that an output voltage of the electromotive force cell 25 reaches a target value, and the pump current becomes a current corresponding to the air-fuel ratio. For that reason, the pump current is detected as a sensor current corresponding to the air-fuel ratio.

Each of the electromotive force cell 25 and the oxygen pump cell 26 includes a solid electrolyte body made of, for example, zirconia, and a pair of electrodes provided on both surfaces of the solid electrolyte body. The two-cell air-fuel ratio sensor 2 includes, as terminals for controlling the air-fuel ratio sensor 2, a terminal 21 connected to one of a pair of electrodes provided in the oxygen pump cell 26, a terminal 22 connected to both of the other of the pair of electrodes provided in the oxygen pump cell 26 and one of a pair of electrodes provided in the electromotive force cell 25, and a terminal 23 connected to the other of the pair of electrodes provided in the electromotive force cell 25.

Also, the one-cell air-fuel ratio sensor 1 may include a label resistor 17, and a terminal 14 connected to one end of the label resistor 17. Similarly, the two-cell air-fuel ratio sensor 2 may include the label resistor 17, and a terminal 24 connected to one end of the label resistor 17.

The label resistors 17 are provided to correct the characteristic variation of the air-fuel ratio sensors 1 and 2, and the resistance values of the label resistors 17 are measured to correct the characteristic variations of the air-fuel ratio sensors 1 and 2. For example, the amount of correction (for example, correction coefficient) for a detected value of a sensor current is determined according to the resistance value of each label resistor 17. The resistance values of the label resistors 17 are set on the basis of the measured characteristics of the air-fuel ratio sensors 1 and 2 during manufacturing of the air-fuel ratio sensors 1 and 2.

Figure 7:
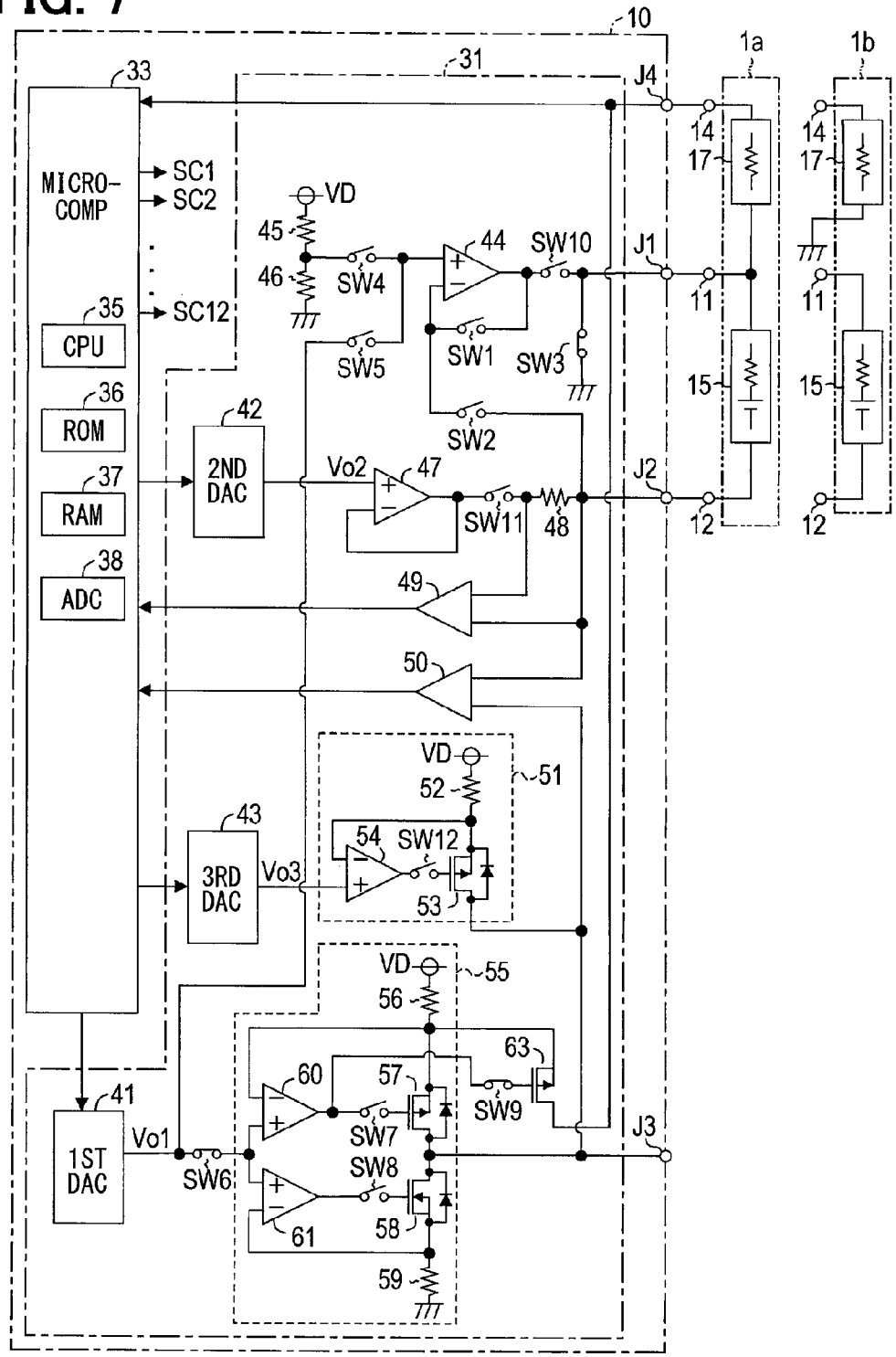
FIG. 7 is a configuration diagram illustrating a circuit state when a one-cell air-fuel ratio sensor having a label resistor is connected to the air-fuel ratio sensor control device, and the control circuit is set in a label resistance measurement mode.

As the one-cell air-fuel ratio sensor 1 having the label resistor 17, there are a one-cell air-fuel ratio sensor 1a (also refer to FIG. 7) of a type in which the other end (a side opposite to the terminal 14 side) of the label resistor 17 is connected to the terminal 11 as illustrated in FIG. 1, and a one-cell air-fuel ratio sensor 1b of a type in which the other end of the label resistor 17 is connected to a ground line as illustrated in FIG. 7.

Figure 5:
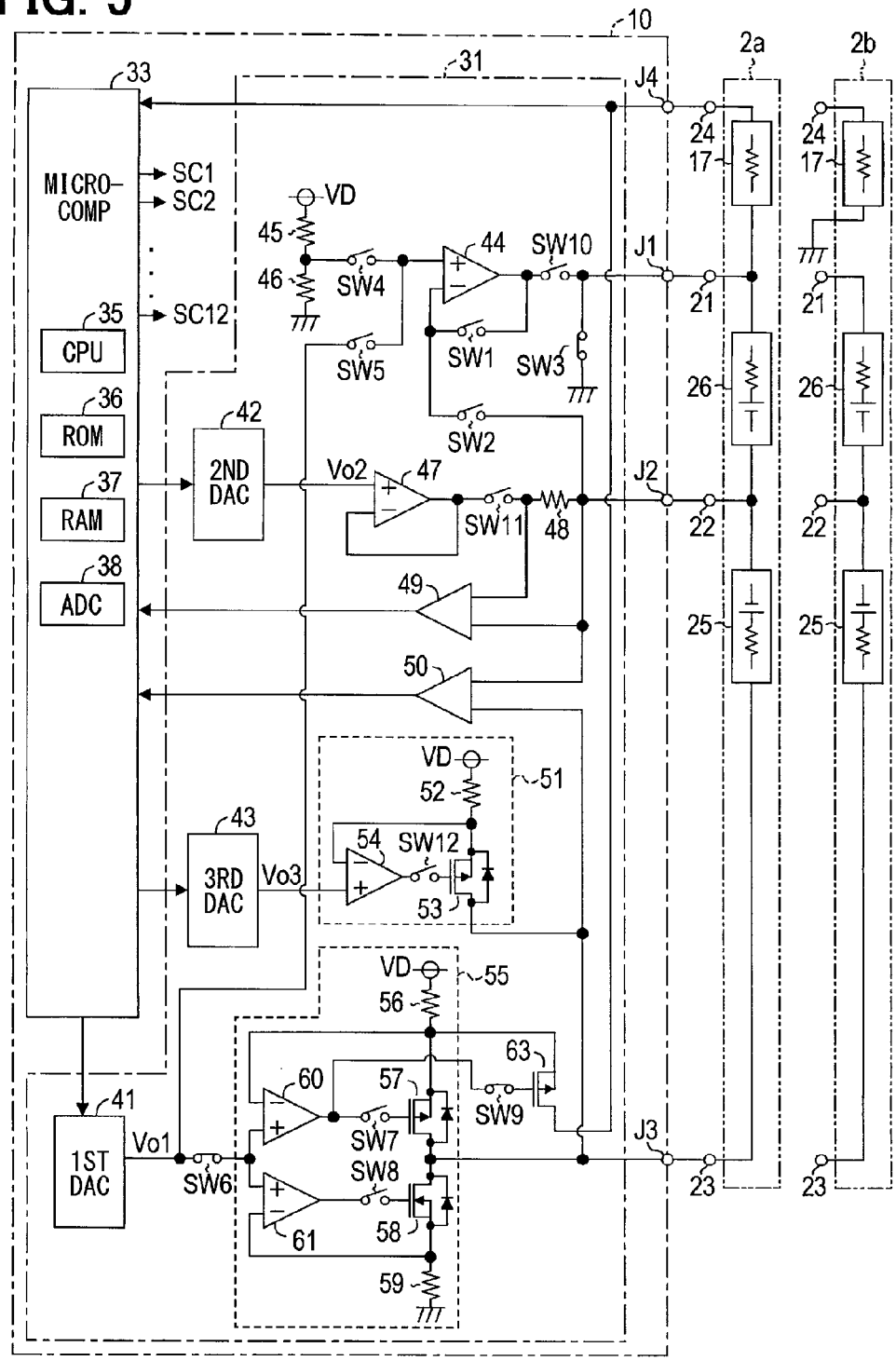
FIG. 5 is a configuration diagram illustrating a circuit state when a two-cell air-fuel ratio sensor having a label resistor is connected to the air-fuel ratio sensor control device, and the control circuit is set in a label resistance measurement mode.

Likewise, as the two-cell air-fuel ratio sensor 2 having the label resistor 17, there are a two-cell air-fuel ratio sensor 2a (also refer to FIG. 5) of a type in which the other end (a side opposite to the terminal 24 side) of the label resistor 17 is connected to the terminal 21 as illustrated in FIG. 1, and a two-cell air-fuel ratio sensor 2b of a type in which the other end of the label resistor 17 is connected to a ground line as illustrated in FIG. 5.

Figure 8:
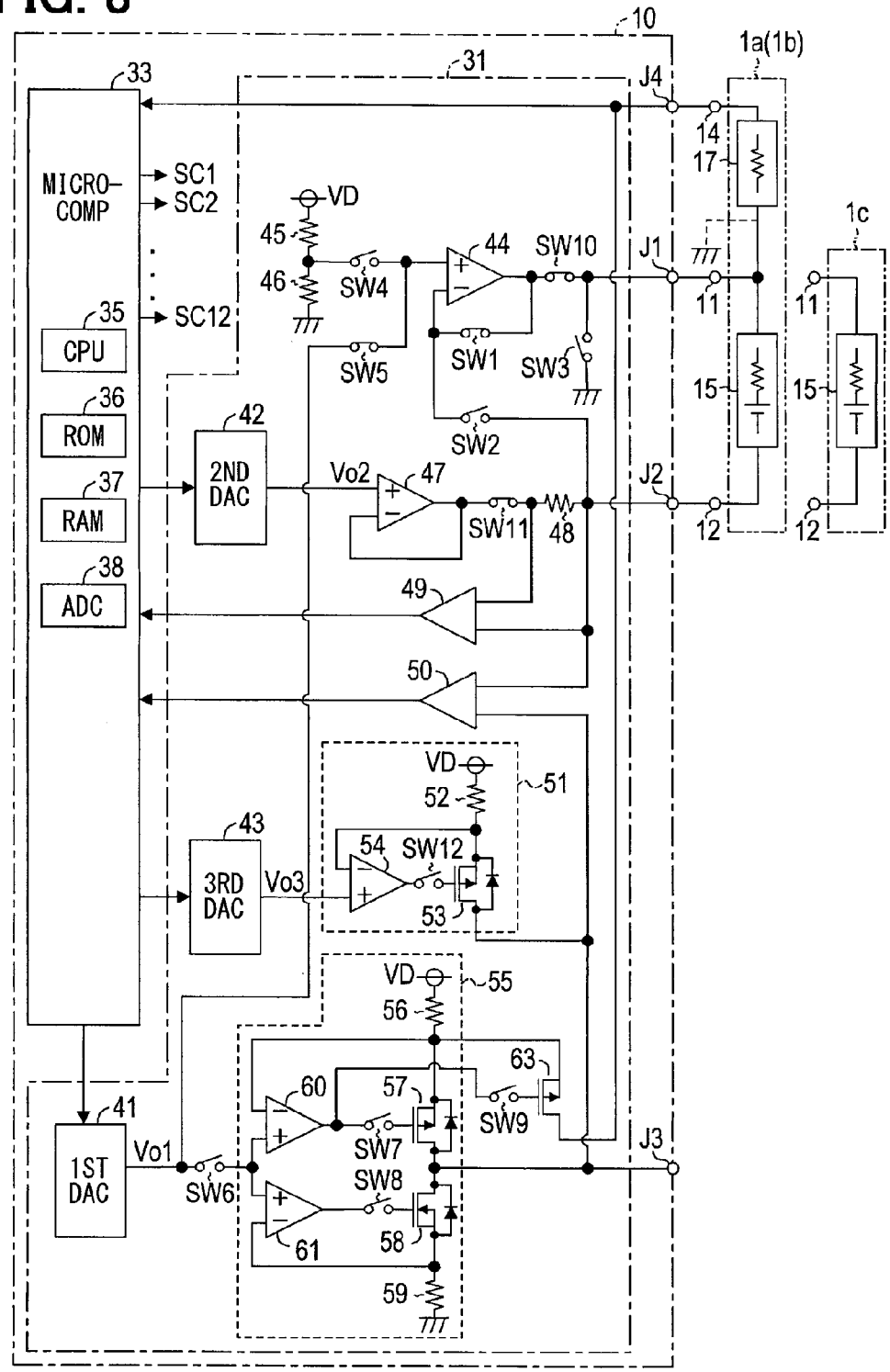
FIG. 8 is a configuration diagram illustrating a circuit state when the one-cell air-fuel ratio sensor is connected to the air-fuel ratio sensor control device, and the control circuit is set in a one-cell mode.
Figure 11:
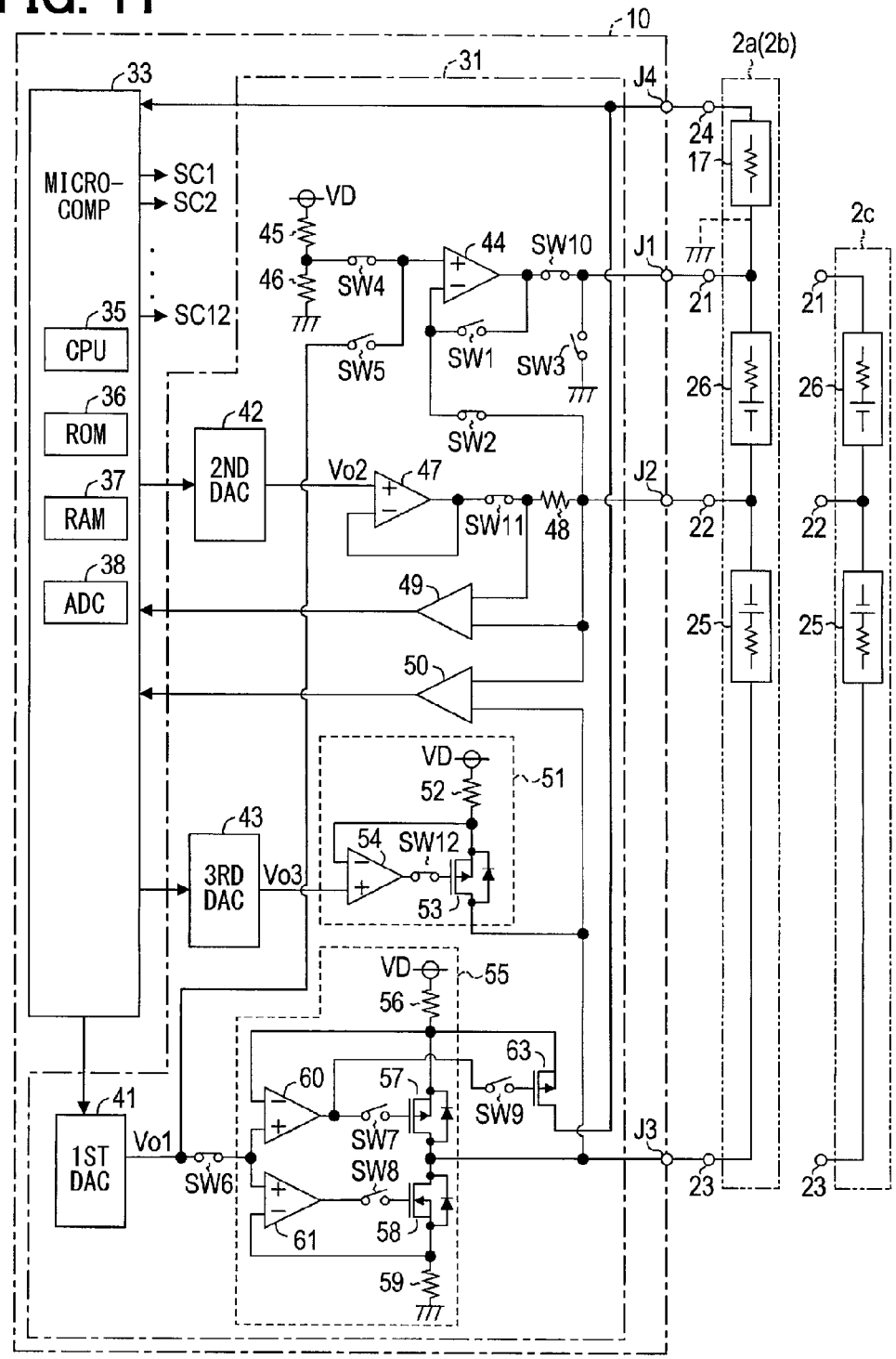
FIG. 11 is a configuration diagram illustrating a circuit state when the two-cell air-fuel ratio sensor is connected to the air-fuel ratio sensor control device, and the control circuit is set in a two-cell mode.

On the other hand, as the one-cell air-fuel ratio sensor 1, as illustrated in FIG. 8, there is also a one-cell air-fuel ratio sensor 1c without the label resistor 17 and the terminal 14. Similarly, as the two-cell air-fuel ratio sensor 2, as illustrated in FIG. 11, there is also a two-cell air-fuel ratio sensor 2c without the label resistor 17 and the terminal 24.

When the one-cell air-fuel ratio sensors 1a, 1b, and 1c are not particularly distinguished, "1" is used as reference numeral, and when the two-cell air-fuel ratio sensors 2a, 2b, and 2c are not particularly distinguished, "2" is used as reference numeral.

The ECU 10 includes four connection terminals J1, J2, J3, and J4 as terminals for connecting any one of the respective air-fuel ratio sensors 1 and 2.

When the two-cell air-fuel ratio sensor 2 is connected to the ECU 10, the terminal 21 is connected to the connection terminal J1, the terminal 22 is connected to the connection terminal J2, and the terminal 23 is connected to the connection terminals J3. When the two-cell air-fuel ratio sensor 2 connected to the ECU 10 is the two-cell air-fuel ratio sensors 2a and 2b each having the label resistor 17, the terminal 24 is connected to the connection terminal J4.

Further, when the one-cell air-fuel ratio sensor 1 is connected to the ECU 10, the terminal 11 is connected to the connection terminal J1, and the terminal 12 is connected to the connection terminal J2. When the one-cell air-fuel ratio sensor 1 connected to the ECU 10 is the one-cell air-fuel ratio sensors 1a and 1b each having the label resistor 17, the terminal 14 is connected to the connection terminal J4.

The ECU 10 includes a control circuit 31 for controlling the air-fuel ratio sensors 1 and 2, and a microcomputer 33 as a controller or a control unit. The microcomputer 33 includes a CPU 35, a ROM 36 in which programs to be executed by the CPU 35, and fixed data are stored, a RAM 37 in which calculation results by the CPU 35 is stored, and an A/D converter (ADC) 38. The operation of the microcomputer 33 to be described below is realized by allowing the CPU 35 to execute the programs within the ROM 36.

The circuit configuration (hereinafter referred to as "mode") of the control circuit 31 can be switched to one of plural types by the microcomputer 33. Specifically, the mode of the control circuit 31 is switched to one of an idle mode in which the connection terminals J1 to J4 are put into a high impedance state, a label resistance measurement mode for measuring the resistance values of the label resistors 17, a two-cell mode (corresponding to a two-cell circuit configuration) for controlling the two-cell air-fuel ratio sensor 2 through the connection terminals J1 to J3, and a one-cell mode (corresponding to a one-cell circuit configuration) for controlling the one-cell air-fuel ratio sensor 1 through the connection terminals J1 and J2.

The control circuit 31 includes a first D/A converter (DAC) 41, a second D/A converter 42, and a third D/A converter 43. Each of the D/A converters 41 to 43 outputs a voltage corresponding to a digital signal as a command from the microcomputer 33.

Also, the control circuit 31 includes an operational amplifier 44, a switch SW10 that turns on to connect an output terminal of the operational amplifier 44 to the connection terminal J1, a switch SW1 that turns on to connect an inverting input terminal and the output terminal of the operational amplifier 44, a switch SW2 that turns on to connect the inverting input terminal of the operational amplifier 44 to the connection terminal J2, a switch SW3 that turns on to connect the connection terminal J1 to a ground line, two series resistors 45 and 46 that divide a constant supply voltage VD (in this example, a supply voltage of the microcomputer 33 and the control circuit 31, for example, 5V) generated within the ECU 10, a switch SW4 that turns on to input a voltage at a connection point of the resistors 45 and 46 to a non-inverting input terminal of the operational amplifier 44, and a switch SW5 that turns on to input an output voltage Vo1 of the first D/A converter 41 to the non-inverting input terminal of the operational amplifier 44.

Also, the control circuit 31 includes an operational amplifier 47 having a non-inverting input terminal to which an output voltage Vo2 of the second D/A converter 42 is input, and an output terminal from which the input voltage is output as a buffer, a current detection resistor 48 having one end connected to the connection terminal J2, a switch SW11 that turns on to connect the other end of the current detection resistor 48 to the output terminal of the operational amplifier 47, an amplifier circuit 49 that outputs a voltage indicative of a voltage difference between both ends of the current detection resistor 48, and an amplifier circuit 50 that outputs a voltage indicative of a voltage difference between the connection terminal J2 and the connection terminal J3. The respective output voltages of the amplifier circuits 49 and 50 are input to the microcomputer 33.

Also, the control circuit 31 includes a current supply circuit 51 for supplying a constant current for allowing the electromotive force cell 25 of the two-cell air-fuel ratio sensor 2 to function (for generating a voltage in the electromotive force cell 25) to the connection terminal J3.

In the current supply circuit 51, a resistor 52 and a transistor 53 are connected between the supply voltage VD and the connection terminal J3 in series in the stated order. In this example, the transistor 53 is formed of a MOSFET, but may be formed of switching elements of other types such as a bipolar transistor or an IGBT (insulated gate bipolar transistor).

The current supply circuit 51 includes an operational amplifier 54, and a switch SW12. The switch SW12 turns on to connect an output terminal of the operational amplifier 54 to a gate of the transistor 53. Also, when the switch SW12 is turned off, the transistor 53 is turned off.

A voltage at a connection point of the resistor 52 and the transistor 53 is input to an inverting input terminal of the operational amplifier 54. Also, an output voltage Vo3 of the third D/A converter 43 is input to a non-inverting input terminal of the operational amplifier 54. When the switch SW12 is on, the operational amplifier 54 turns on the transistor 53 so that the voltage at the connection point of the resistor 52 and the transistor 53 matches the output voltage Vo3 of the third D/A converter 43.

For that reason, when it is assumed that a resistance value of the resistor 52 is R52, a current of "(VD−Vo3)/R52" is supplied to the connection terminal J3 by the current supply circuit 51.

Also, the control circuit 31 includes a current supply circuit 55 for supplying a constant current for measuring an impedance of the electromotive force cell 25 in the two-cell air-fuel ratio sensor 2 to the connection terminal J3, and a switch SW6.

In the current supply circuit 55, a resistor 56, a transistor 57, a transistor 58, and a resistor 59 are connected between the supply voltage VD and the ground line in series in the stated order. A connection point between the transistor 57 and the transistor 58 is connected to the connection terminal J3. In this example, each of the transistors 57 and 58 is formed of a MOSFET, but may be formed of switching elements of other types such as a bipolar transistor or an IGBT.

The current supply circuit 55 includes operational amplifiers 60, 61, and switches SW7, SW8. The switch SW7 turns on to connect an output terminal of the operational amplifier 60 to a gate of the transistor 57. Also, when the switch SW7 is turned off, the transistor 57 is turned off. Likewise, the switch SW8 turns on to connect an output terminal of the operational amplifier 61 to a gate of the transistor 58. Also, when the switch SW8 is turned off, the transistor 58 is turned off.

A voltage at a connection point of the resistor 56 and the transistor 57 is input to an inverting input terminal of the operational amplifier 60. A voltage at a connection point of the resistor 59 and the transistor 58 is input to an inverting input terminal of the operational amplifier 61. Also, the switch SW6 is turned on, as a result of which the output voltage Vo1 of the first D/A converter 41 is input to non-inverting input terminals of the operational amplifiers 60 and 61.

When the switches SW6 and SW7 are on, the operational amplifier 60 turns on the transistor 57 so that the voltage at the connection point of the resistor 56 and the transistor 57 matches the output voltage Vo1 of the first D/A converter 41. Likewise, when the switch SW6 and the switch SW8 are on, the operational amplifier 61 turns on the transistor 58 so that the voltage at the connection point of the resistor 59 and the transistor 58 matches the output voltage Vo1 of the first D/A converter 41.

For that reason, when it is assumed that a resistance value of the resistor 56 is R56, the switch SW6 and the switch SW7 are turned on, as a result of which a current of "(VD−Vo1)/R56" is supplied to the connection terminal J3 in a direction of flowing the current into the connection terminal J3. Hereinafter, this current is called "+Iz". Also, when it is assumed that a resistance value of the resistor 59 is R59, the switch SW6 and the switch SW8 are turned on, as a result of which a current of "Vo1/R59" is supplied to the connection terminal J3 in a direction of drawing the current from the connection terminal J3. Hereinafter, this current is called "−Iz".

Also, the control circuit 31 includes a transistor 63 and a switch SW9 which supply a current (hereinafter referred to as "label resistance measurement current") for supplying a resistance value of the label resistor 17 to the connection terminal J4 in cooperation with the resistor 56 and an operational amplifier 60 configuring the current supply circuit 55. In this example, the transistor 63 is formed of a MOSFET, but may be formed of switching elements of other types such as a bipolar transistor or an IGBT.

The transistor 63 is disposed between an end of the resistor 56 opposite to the supply voltage VD side and the connection terminal J4, and the switch SW9 is turned on, as a result of which a gate of the transistor 63 is connected to an output terminal of the operational amplifier 60. Also, when the switch SW9 is turned off, the transistor 63 is turned off.

When the switch SW6 and the switch SW9 are on, the operational amplifier 60 turns on the transistor 63 so that the voltage at the connection point of the resistor 56 and the transistor 63 matches the output voltage Vo1 of the first D/A converter 41.

For that reason, the switch SW6 and the switch SW9 are turned on, as a result of which the current of "(VD−Vo1)/R56" is supplied to the connection terminal J4 as the label resistance measurement current. A voltage of the connection terminal J4 is input to the microcomputer 33.

The respective switches SW1 to SW12 switch on/off according to control signals SC1 to SC12 from the microcomputer 33. In this embodiment, the respective switches SW1 to SW12 are turned on when the corresponding control signals SC1 to SC12 are high.

Then, the switches SW1 to SW12 change over to on/off states as illustrated in FIG. 2, to thereby set a mode of the control circuit 31 to any one of the idle mode, the label resistance measurement mode, the one-cell mode, and the two-cell mode. In the two-cell mode, the switch SW7 and the switch SW8 are turned on/off at the time of measuring the impedance of the electromotive force cell 25.

Figure 3:
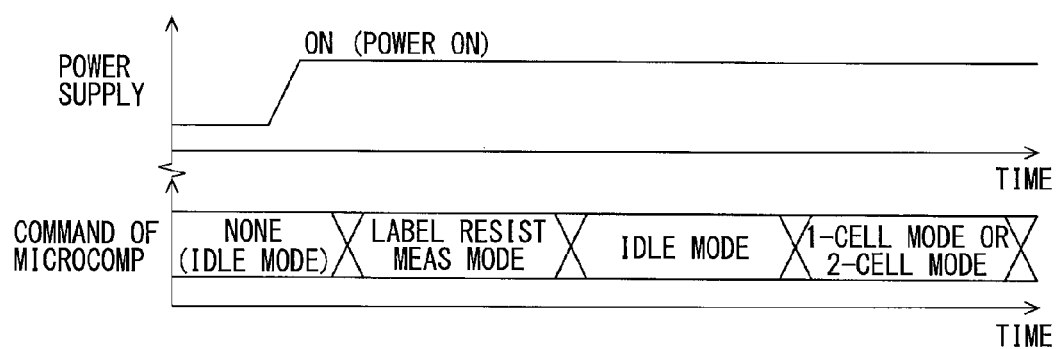
FIG. 3 is an illustrative view illustrating a change in the modes of the control circuit after a power is supplied to the air-fuel ratio sensor control device.

Also, as illustrated in FIG. 3, the mode of the control circuit 31 becomes the idle mode at the time of supplying a power to the ECU 10 for operation. When an ignition switch of a vehicle is turned on, a vehicle battery voltage is applied to the ECU 10 as the power supply for the operation.

Figure 4:
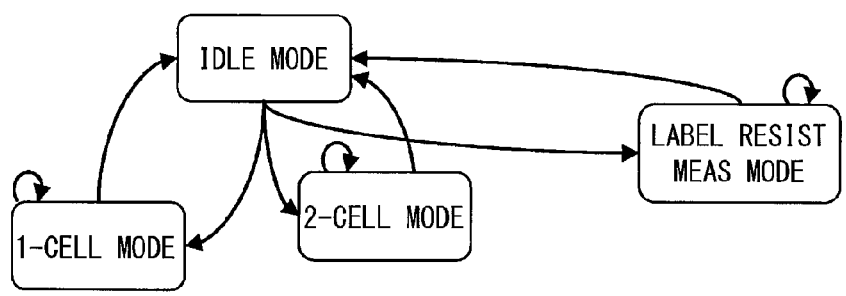
FIG. 4 is an illustrative view illustrating the transition of the modes of the control circuit.

The microcomputer 33 that has started by powering on the ECU 10 outputs the control signals SC1 to SC12 to the respective switches SW1 to SW12, to thereby switch over the mode of the control circuit 31 to a mode other than the idle mode. Also, as illustrated in FIGS. 3 and 4, when changing the mode of the control circuit 31, the microcomputer 33 switches to another mode after returning to the idle mode once.

When the one-cell air-fuel ratio sensors 1a and 1b, or the two-cell air-fuel ratio sensors 2a and 2b each having the label resistor 17 are connected to the ECU 10, if the microcomputer 33 starts by powering on the ECU 10 as illustrated in FIG. 3, the microcomputer 33 switches the mode of the control circuit 31 from the idle mode to the label resistance measurement mode, and measures the resistance value of the label resistor 17. Then, upon completion of measuring the resistance value of the label resistor 17, the microcomputer 33 returns the mode of the control circuit 31 to the idle mode. Thereafter, the microcomputer 33 switches the mode of the control circuit 31 to the one-cell mode if the one-cell air-fuel ratio sensors 1a and 1b are connected to the ECU 10, and also switches the mode of the control circuit 31 to the two-cell mode if the two-cell air-fuel ratio sensors 2a and 2b are connected to the ECU 10.

Further, when the one-cell air-fuel ratio sensor 1c or the two-cell air-fuel ratio sensor 2c each having no label resistor 17 is connected to the ECU 10, when the microcomputer 33 starts by powering on the ECU 10, the microcomputer 33 switches the mode of the control circuit 31 to not the label resistance measurement mode, but the one-cell mode or the two-cell mode.

Subsequently, a description will be given of the circuit configuration and the operation in the respective modes of the control circuit 31, and the processing contents of the microcomputer 33 in the respective modes.

<Idle Mode>

As illustrated in FIG. 2, the mode of the control circuit 31 becomes the idle mode when all of the switches SW1 to SW12 are off.

Even if the power is supplied to the ECU 10, because all of the control signals SC1 to SC12 are low until the microcomputer 33 starts to make one of the control signals SC1 to SC12 high, the mode of the control circuit 31 becomes the idle mode. Then, in the idle mode, since at least the switches SW3, and SW7 to SW12 are off, the connection terminals J1 to J4 become in a high impedance state (release state). For that reason, an unnecessary voltage is prevented from being output from the connection terminals J1 to J4 immediately after powering on the ECU 10. As described above, when the switches SW7 to SW9, and SW12 are off, the transistors 53, 57, 58, and 63 turn off.

<Label Resistance Measurement Mode>

As illustrated in FIG. 2, when the switches SW3, SW6, and SW9 of the switches SW1 to SW12 are turned on, the mode of the control circuit 31 becomes the label resistance measurement mode.

Figure 6:
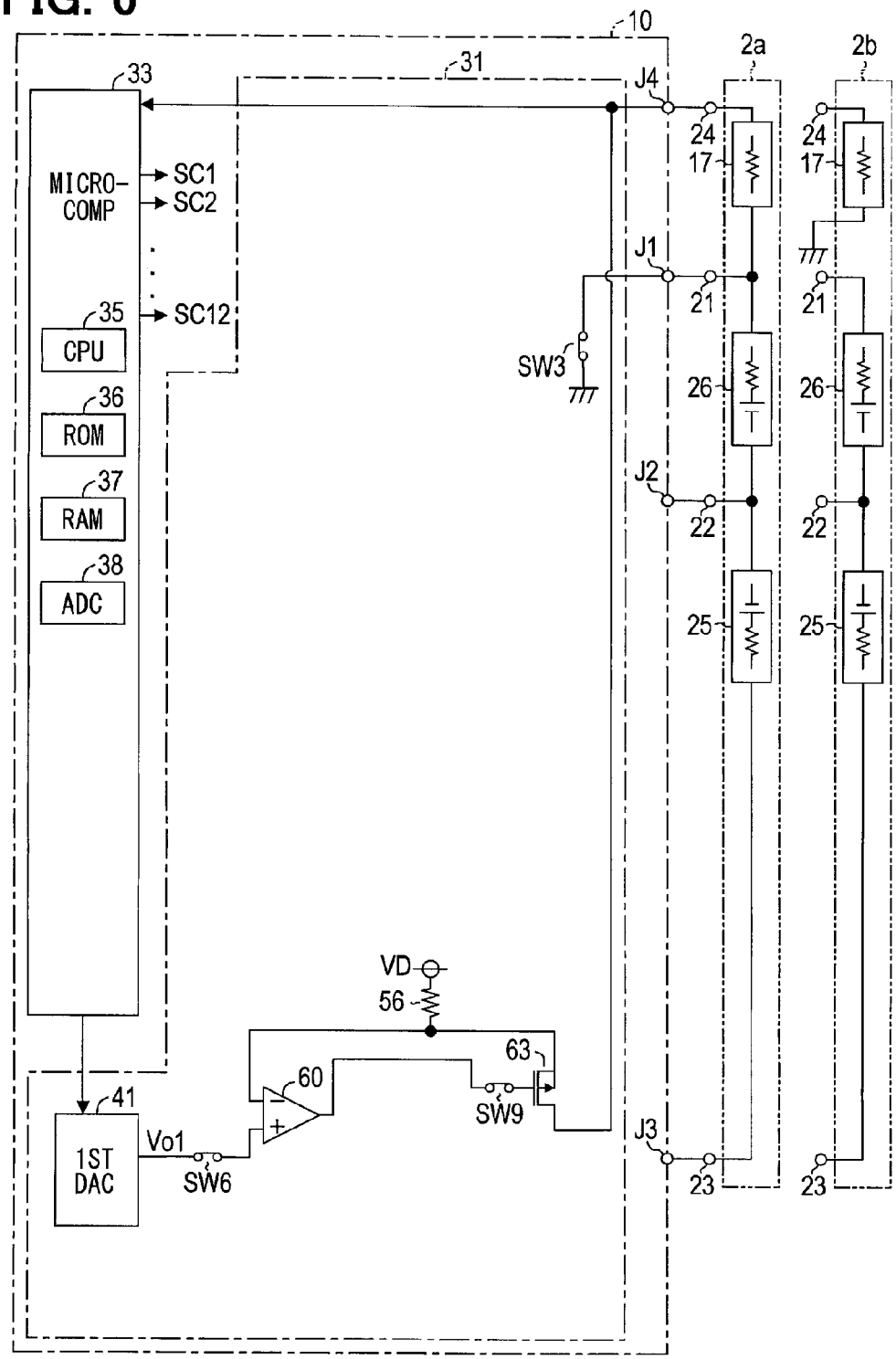
FIG. 6 is a configuration diagram illustrating only components that function in the label resistance measurement mode among components of the control circuit in FIG. 5.

FIG. 5 illustrates a circuit state when the two-cell air-fuel ratio sensor 2a having the label resistor 17 is connected to the ECU 10, and the mode of the control circuit 31 is set in the label resistance measurement mode. FIG. 6 illustrates only components that function in the label resistance measurement mode in components of the control circuit 31 in FIG. 5.

Referring to FIGS. 5 and 6, in the case of the label resistance measurement mode, the above-mentioned current of "(VD−Vo1)/R56" flows as a label resistance measurement current in a route of the transistor 63, the connection terminal J4, the label resistor 17, the connection terminal J1, the switch SW3, and the ground line in the stated order.

For that reason, when the mode of the control circuit 31 is set to the label resistance measurement mode, the microcomputer 33 controls the output voltage Vo1 of the first D/A converter 41 so that the label resistance measurement current becomes an appropriate value (that is, the voltage of the connection terminal J4 becomes a readable voltage). Then, the microcomputer 33 detects the voltage of the connection terminal J4 by the A/D converter 38, and calculates the resistance value of the label resistor 17 according to the detected voltage. When the detected voltage of the connection terminal J4 is divided by the label resistance measurement current, the resistance value of the label resistor 17 can be calculated. Calculating the resistance value of the label resistor 17 corresponds to measuring the resistance value.

In addition, the microcomputer 33 determines a correction amount for the detected value of the sensor current on the basis of the measured resistance value of the label resistor 17. For example, a correspondence relationship between the resistance value of the label resistor 17 and the correction amount for the sensor current is stored in the ROM 36, and the measured resistance value is applied to the correspondence relationship to determine the correction amount used at the time of detecting the sensor current.

In FIGS. 5 and 6, as illustrated on a right side of the two-cell air-fuel ratio sensor 2a, when the two-cell air-fuel ratio sensor 2b of the type in which a side of the label resistor 17 opposite to the terminal 24 side is connected to the ground line is connected to the ECU 10, a current flows into the label resistor 17 without passing through the switch SW3 differently from the above case. In this case, the switch SW3 may be configured not to be turned on, but the switch SW3 can be turned on without any problem.

Also, FIG. 7 illustrates a circuit state when the one-cell air-fuel ratio sensor 1a (or 1b) having the label resistor 17 is connected to the ECU 10, and the mode of the control circuit 31 is set in the label resistance measurement mode. Likewise, in this case, the circuit configuration of the control circuit 31 is identical with that of FIGS. 5 and 6, and conducts the same operation and processing as those when the two-cell air-fuel ratio sensors 2a and 2b are connected to the ECU 10.

(One-Cell Mode)

As illustrated in FIG. 2, when the switches SW1, SW5, SW10, and SW11 of the switches SW1 to SW12 turn on, the mode of the control circuit 31 becomes the one-cell mode.

Figure 9:
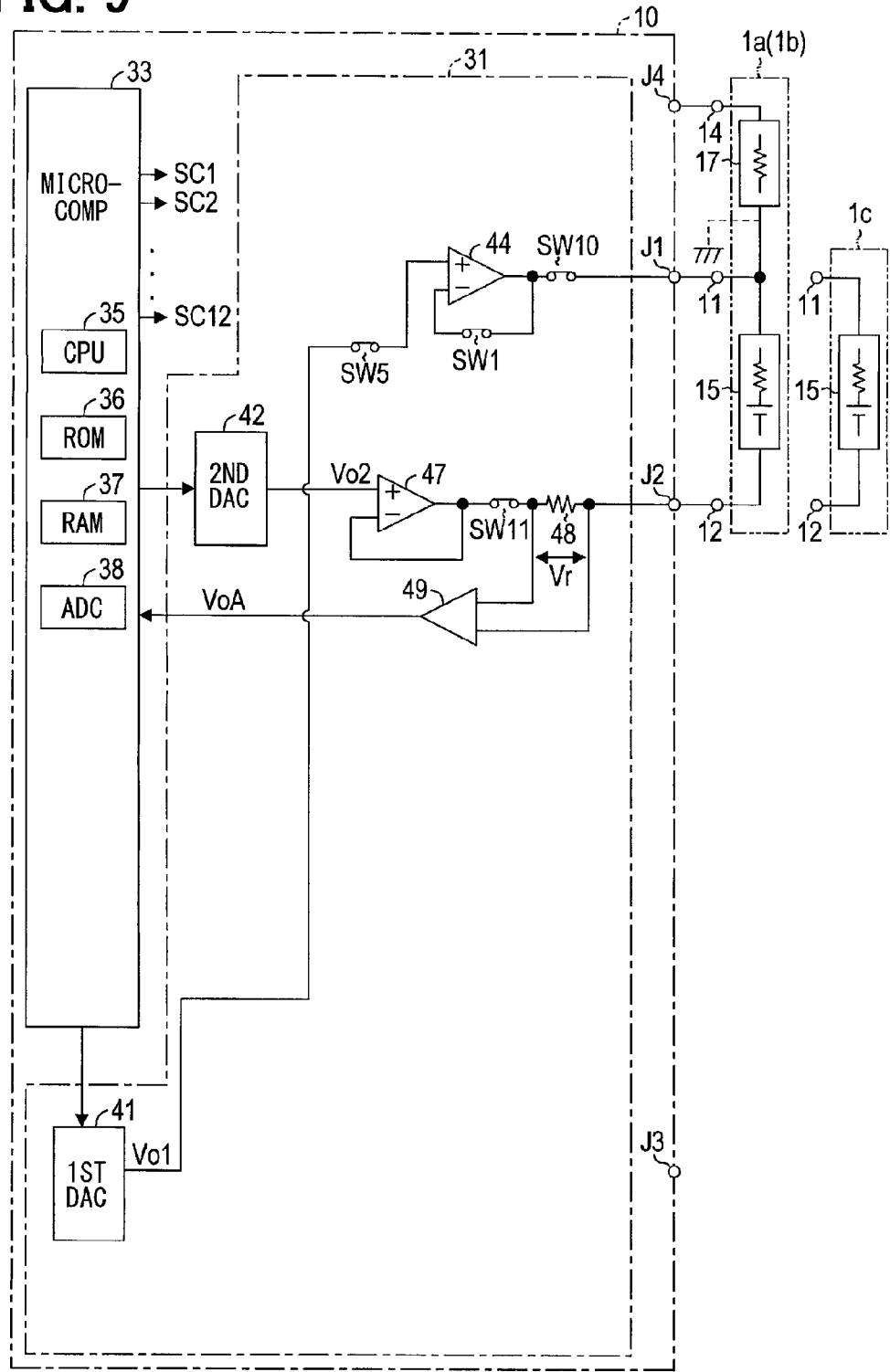
FIG. 9 is a configuration diagram illustrating only components that function in the one-cell mode in components of the control circuit in FIG. 8.

FIG. 8 illustrates a circuit state when the one-cell air-fuel ratio sensor 1 is connected to the ECU 10, and the mode of the control circuit 31 is set to the one-cell mode. FIG. 9 illustrates only components that function in the one-cell mode in components of the control circuit 31 in FIG. 8. FIGS. 8 and 9 illustrate a state in which the one-cell air-fuel ratio sensor 1a is connected to the ECU 10. However, in the case where referring to FIGS. 8 and 9, the one-cell air-fuel ratio sensor 1b in which one end of the label resistor 17 is connected to the ground line is connected to the ECU 10 as indicated by a symbol in parentheses, and a dotted line below the label resistor 17, or in the case where referring to FIGS. 8 and 9, the one-cell air-fuel ratio sensor 1c is connected to the ECU 10 as indicated by a right side of the one-cell air-fuel ratio sensor 1a (1b), the same operation and processing are conducted.

As illustrated in FIG. 9, in the case of the one-cell mode, because the switch SW1 of the switches SW1 and SW2 is turned on, the operational amplifier 44 functions as a buffer that outputs the output voltage Vo1 of the first D/A converter 41. The output terminal of the operational amplifier 44 is connected to the terminal 11 of the one-cell air-fuel ratio sensor 1 through the connection terminal J1. For that reason, the output voltage Vo1 of the first D/A converter 41 is applied to one electrode (electrode on the terminal 11 side) of the cell 15.

Also, the output voltage Vo2 of the second D/A converter 42 is applied to a side of the current detection resistor 48 opposite to the connection terminal J2 side through the operational amplifier 47 as the buffer. The connection terminal J2 side of the current detection resistor 48 is connected to the terminal 12 of the one-cell air-fuel ratio sensor 1 through the connection terminal J2. For that reason, the output voltage Vo2 of the second D/A converter 42 is applied to an electrode of the cell 15 on the terminal 12 side through the current detection resistor 48.

The same current as the current flowing into the cell 15 flows into the current detection resistor 48, and a voltage indicative of a voltage difference between both ends of the current detection resistor 48, which is a voltage indicative of a current flowing into the cell 15, is input to the microcomputer 33 from the amplifier circuit 49.

The microcomputer 33 controls the first D/A converter 41 and the second D/A converter 42, to thereby apply an AC-varying voltage to the cell 15. The microcomputer 33 detects a DC component of the current flowing into the current detection resistor 48 as a sensor current corresponding to the air-fuel ratio, and detects the impedance of the cell 15 from an AC component of the current flowing into the current detection resistor 48.

The processing content of the microcomputer 33 will be described in more detail.

Figure 10:
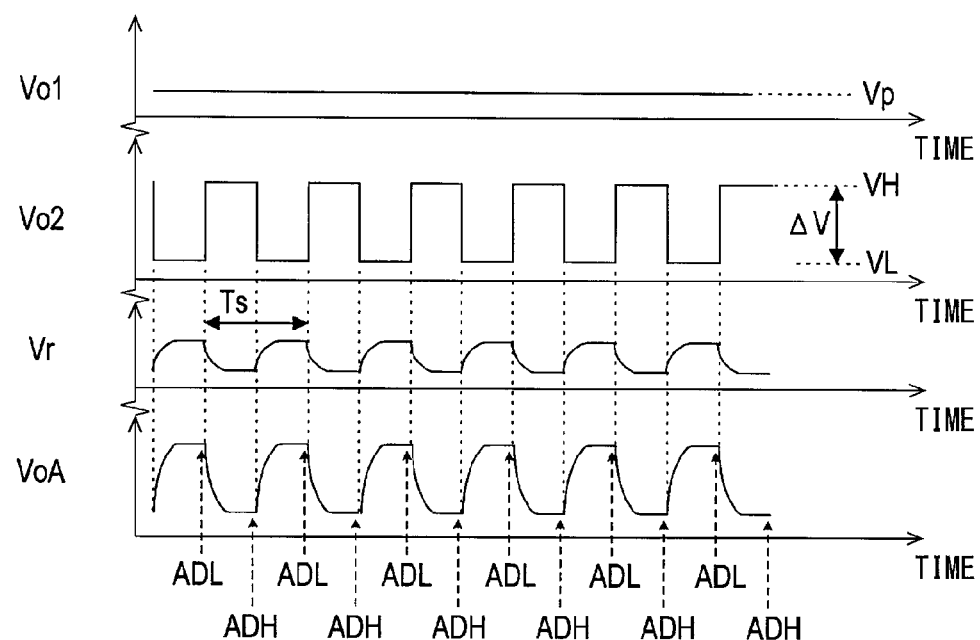
FIG. 10 is an illustrative view illustrating a processing content of a microcomputer when the control circuit is in the one-cell mode.

As indicated in a first row of FIG. 10, the microcomputer 33 sets the output voltage Vo1 of the first D/A converter 41 to a constant voltage Vp. The voltage Vp may be a fixed value, or may change according to the sensor current.

Also, as indicated in a second row of FIG. 10, the microcomputer 33 alternately switches the output voltage Vo2 of the second D/A converter 42 to a first voltage VH and a second voltage VL which are different from the above voltage Vp in a predetermined period Ts. The output voltage Vo2 becomes the first voltage VH in one half of the period Ts, and the second voltage VL in the other half thereof. For example, a magnitude relationship of "Vp>VH>VL" is met. The first voltage VH and the second voltage VL thus switched are applied to a side of the current detection resistor 48 opposite to the cell 15 side.

For example, when it is assumed that the voltage Vp is 2.9 V, the first voltage VH is 2.7 V, and the second voltage VL is 2.3 V, a mean value of applied voltages to a series circuit of the cell 15 and the current detection resistor 48 becomes 0.4 V (=2.9 V−(2.7 V+2.3 V)/2). Also, a difference $\Delta V$ between the first voltage VH and the second voltage VL becomes 0.4 V (=2.7 V−2.3 V), and the difference $\Delta V$ becomes a variation width of changing the applied voltage in an AC manner. The reason that the applied voltage changes by the difference $\Delta V$ in the AC manner is to detect the impedance (AC resistance) of the cell 15.

As indicated in the second row and a fourth row of FIG. 10, the microcomputer 33 subjects an output voltage VoA (refer to FIG. 9) of the amplifier circuit 49 to A/D conversion every immediately prior to switching the output voltage Vo2 of the second D/A converter 42 from one of the first voltage VH and the second voltage VL to the other.

Referring to FIG. 10, upward dotted arrows indicate A/D conversion timing of the output signal VoA of the amplifier circuit 49. In FIG. 10 and the following description, "ADH" is an A/D conversion result when the output voltage Vo2 of the second D/A converter 42 is the first voltage VH, and in more detail, an A/D conversion result immediately before the output voltage Vo2 switches from the first voltage VH to the second voltage VL. Also, in FIG. 10 and the following description, "ADL" is an A/D conversion result when the output voltage Vo2 of the second D/A converter 42 is the second voltage VL, and in more detail, an A/D conversion result immediately before the output voltage Vo2 switches from the second voltage VL to the first voltage VH. On the other hand, "Vr" in a third row of FIG. 10 represents a voltage difference (refer to FIG. 9) between both ends of the current detection resistor 48. Also, referring to FIG. 10, in "Vr" and "VoA", a direction from the cell 15 side toward the operational amplifier 47 side of directions of the current flowing into the current detection resistor 48 is positive, and a value becomes larger as the current in the positive direction is larger.

The microcomputer 33 calculates a sensor current Is and an impedance Z of the cell 15 with the use of two consecutive A/D conversion results (that is, ADH and ADL where the A/D conversion timing is consecutive).

Specifically, the microcomputer 33 calculates the sensor current Is through the following Expression 1. In the expression, "G" is a gain (amplification degree) of the amplifier circuit 49, and "Rs" is a resistance value of the current detection resistor 48.

$$Is=(ADH+ADL)/2/G/Rs \quad \text{Ex. 1}$$

In other words, the microcomputer 33 averages the ADH and ADL where the A/D conversion timing is consecutive, and calculates the sensor current Is corresponding to the air-fuel ratio according to the averaged value. Then, the microcomputer 33 applies the calculated sensor current Is to a predetermined expression or data map to convert the sensor current Is into the air-fuel ratio. If the microcomputer 33 measures the resistance value of the label resistor 17 to determine the correction amount of the sensor current, the microcomputer 33 corrects the sensor current Is calculated through Expression 1 with the use of the correction amount, and calculates the air-fuel ratio according to the corrected sensor current. The air-fuel ratio thus calculated is used for an air-fuel ratio feedback control of an internal combustion engine.

Also, the microcomputer 33 calculates the impedance Z of the cell 15 through the following Expression 2.

$$Z=\{G \times \Delta V-(ADL-ADH)\} \times Rs/(ADL-ADH) \quad \text{Ex. 2}$$

That is, the microcomputer 33 calculates the impedance Z according to a difference between ADH and ADL where the A/D conversion timing is consecutive.

"ΔV" in Expression 2 is "VH−VL". Expression 2 derives from the following Expressions 3 and 4. Also, in Expressions 2 to 4, like the third row and the fourth row in FIG. 10, a direction from the cell 15 side toward the operational amplifier 47 side of directions of the current flowing into the current detection resistor 48 is positive, and the output voltage VoA of the amplifier circuit 49 becomes larger as the current in the positive direction is larger.

$$ADH=G \times (Vp-VH) \times Rs/(Rs+Z) \quad \text{Ex. 3}$$

$$ADL=G \times (Vp-VL) \times Rs/(Rs+Z) \quad \text{Ex. 4}$$

Because the impedance Z of the cell 15 has a correlation with the temperature of the cell 15, the microcomputer 33 determines whether the cell 15 is in an active state, or not, or controls a heater (not shown) for heating the cell 15, on the basis of the calculated impedance Z.

On the other hand, as another example, the microcomputer 33 may subject the output voltage VoA of the amplifier circuit 49 to processing of a low-pass filter and a high-pass filter, and calculate the impedance Z of the cell 15 from a value obtained by peak holding an output result of the high-pass filter with an output result of the low-pass filter as the sensor current Is.

(Two-Cell Mode)

As illustrated in FIG. 2, when the switches SW2, SW4, SW6, and SW10 to SW12 of the switches SW1 to SW12 are turned on, the mode of the control circuit 31 becomes the two-cell mode.

Figure 12:
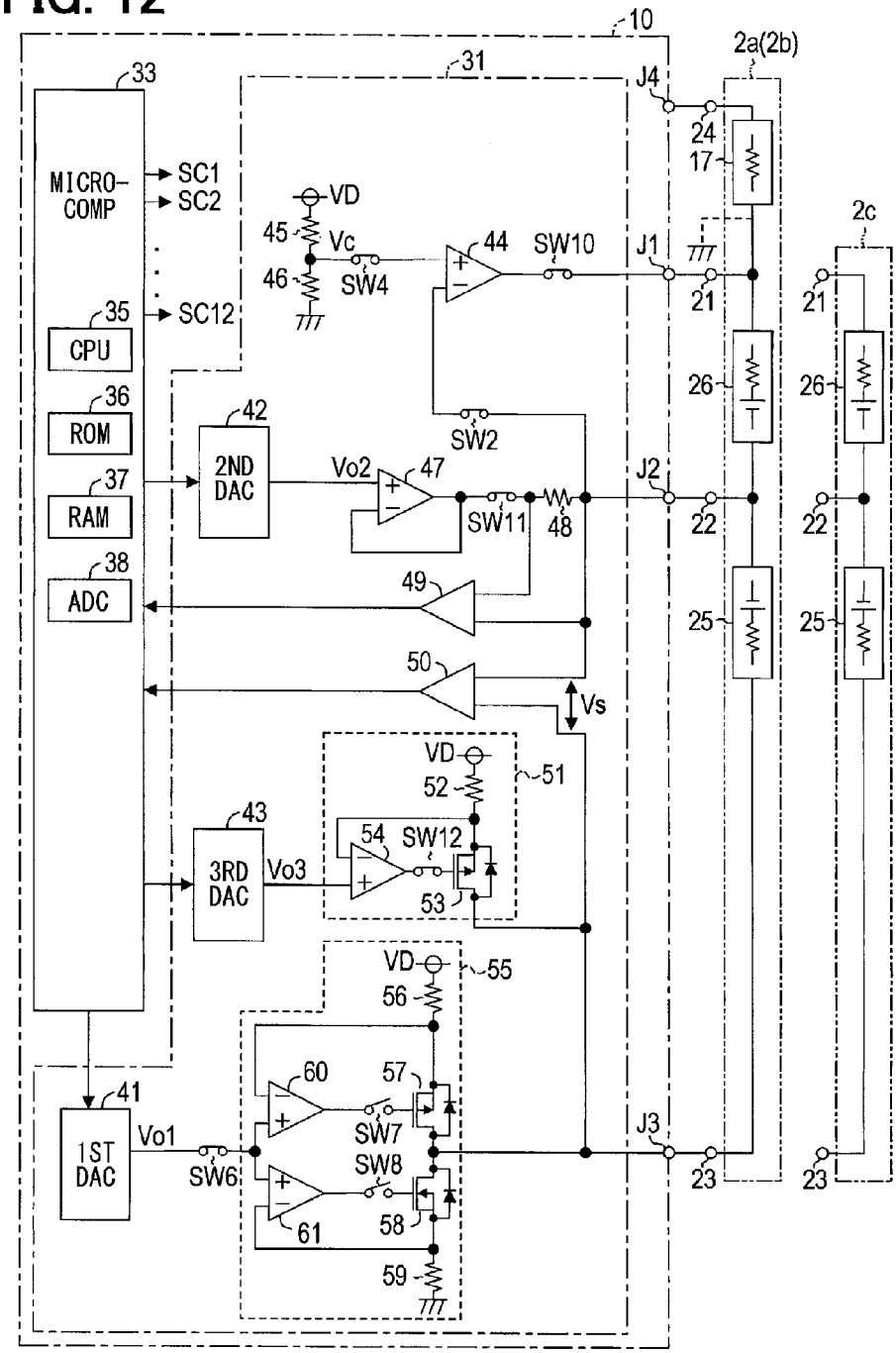
FIG. 12 is a configuration diagram illustrating only components that function in the two-cell mode among components of the control circuit in FIG. 11.

FIG. 11 illustrates a circuit state when the two-cell air-fuel ratio sensor 2 is connected to the ECU 10, and the mode of the control circuit 31 is set to the two-cell mode. FIG. 12 illustrates only components that function in the two-cell mode in components of the control circuit 31 in FIG. 11. FIGS. 11 and 12 illustrate a state in which the two-cell air-fuel ratio sensor 2a is connected to the ECU 10. However, in the case where referring to FIGS. 11 and 12, the two-cell air-fuel ratio sensor 2b in which one end of the label resistor 17 is connected to the ground line is connected to the ECU 10 as indicated by a symbol in parentheses, and a dotted line below the label resistor 17, or in the case where referring to FIGS. 11 and 12, the two-cell air-fuel ratio sensor 2c is connected to the ECU 10 as indicated by a right side of the two-cell air-fuel ratio sensor 2a (2b), the same operation and processing are conducted.

As illustrated in FIG. 12, in the case of the two-cell mode, because the switch SW2 of the switches SW1 and SW2 is turned on, the inverting input terminal of the operational amplifier 44 is connected to the terminal 22 of the two-cell air-fuel ratio sensor 2 through the connection terminal J2. Also, the output terminal of the operational amplifier 44 is connected to the terminal 21 of the two-cell air-fuel ratio sensor 2 through the connection terminal J1.

For that reason, the operational amplifier 44 outputs a voltage to the terminal 21 so that a voltage input to the non-inverting input terminal of the operational amplifier 44 matches the voltage of the terminal 22. Also, a voltage Vc (for example, 2.5V) at a connection point of the resistors 45 and 46 is input to the non-inverting input terminal of the operational amplifier 44 through the switch SW4. Hence, the operational amplifier 44 outputs the voltage to the terminal 21 so that the voltage of the terminal 22 reaches the voltage Vc.

Also, like the one-cell mode, in the two-cell mode, the output voltage Vo2 of the second D/A converter 42 is applied to a side of the current detection resistor 48 opposite to the connection terminal J2 side through the operational amplifier 47 as the buffer. The connection terminal J2 side of the current detection resistor 48 is connected to the terminal 22 of the two-cell air-fuel ratio sensor 2 through the connection terminal J2.

For that reason, a pump current flows into the oxygen pump cell 26 due to the operational amplifier 44 and the operational amplifier 47, and the pump current flows into the current detection resistor 48. Then, a voltage indicative of a voltage difference between both ends of the current detection resistor 48, which is a voltage indicative of the pump current, is input to the microcomputer 33 from the amplifier circuit 49.

Also, a constant current for allowing the electromotive force cell 25 to function is supplied to the terminal 23 of the two-cell air-fuel ratio sensor 2 from the current supply circuit 51 through the connection terminal J3.

The microcomputer 33 controls the output voltage Vo3 of the third D/A converter 43 so that the output current (the above-mentioned "(VD−Vo3)/R52") of the current supply circuit 51 becomes an optimum value of the two-cell air-fuel ratio sensor 2 connected to the ECU 10.

Also, a voltage between both ends of the electromotive force cell 25 (voltage between the terminals 23 and 22) is applied to the microcomputer 33 from the amplifier circuit 50 as an inter-sensor voltage Vs.

The microcomputer 33 controls the output voltage Vo2 of the second D/A converter 42 (that is, the output voltage to the current detection resistor 48) so that the inter-sensor voltage Vs becomes the target value (for example, 0.45 V).

With the above configuration, the pump current flowing into the oxygen pump cell 26 is controlled so that the inter-sensor voltage Vs which is the output voltage of the electromotive force cell 25 becomes the target value, and the pump current flows into the current detection resistor 48 as the sensor current indicative of the air-fuel ratio.

For that reason, the microcomputer 33 detects the sensor current on the basis of the voltage input from the amplifier circuit 49, and applies the detected sensor current to a predetermined expression or data map, to thereby convert the sensor current into the air-fuel ratio. When the microcomputer 33 measures the resistance value of the label resistor 17 to determine the correction amount of the sensor current, the microcomputer 33 corrects the detected sensor current with the use of the correction amount, and calculates the air-fuel ratio according to the corrected sensor current. The air-fuel ratio thus calculated is used for an air-fuel ratio feedback control of an internal combustion engine.

Also, in the case of the two-cell mode, the output voltage Vo1 of the first D/A converter 41 is input to the non-inverting input terminals of the operational amplifiers 60 and 61 in the current supply circuit 55.

Figure 13:
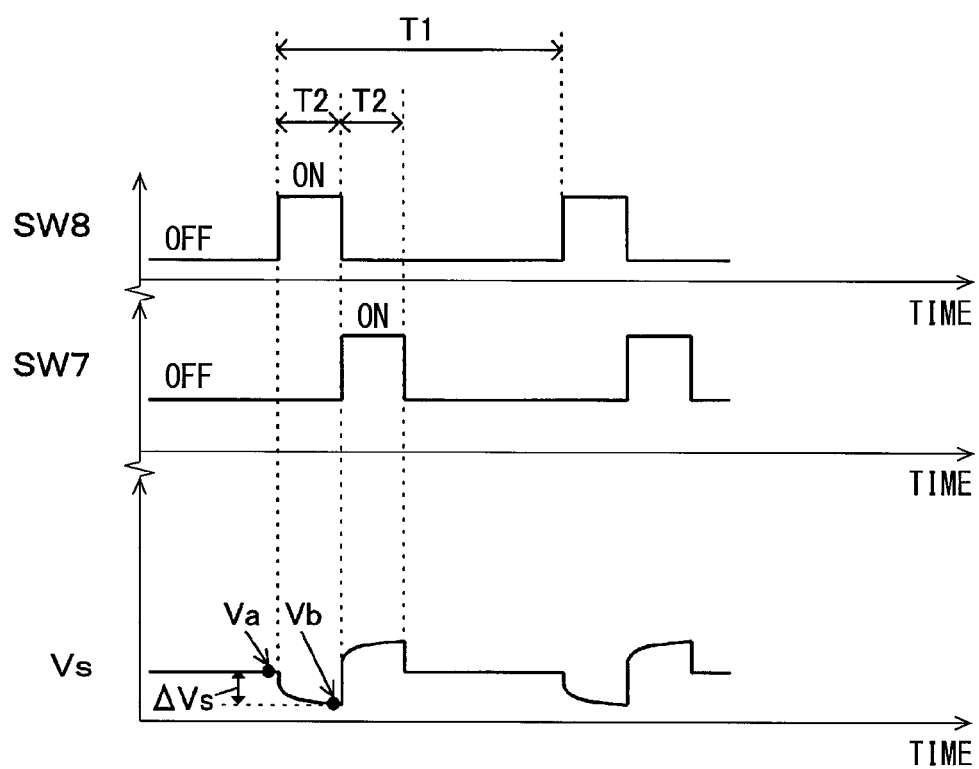
FIG. 13 is an illustrative view illustrating a processing content of a microcomputer when the control circuit is in the two-cell mode.

As indicated in a first row and a second row of FIG. 13, the microcomputer 33 turns on the switch SW7 for a predetermined time T2 after turning on, for example, the switch SW8 of the switches SW7 and SW8 for the predetermined time T2, and then switching the switch SW8 from on to off, every predetermined time T1. For that reason, the current supply circuit 55 supplies the above-mentioned "−Iz" to the electromotive force cell 25 every predetermined time T1, and after completion of the supply of the "−Iz", supplies "+Iz" opposite in a direction to the "−Iz" to the electromotive force cell 25. The predetermined time T1 is a period during which the impedance Z of the electromotive force cell 25 is detected.

In addition, the microcomputer 33 controls the output voltage Vo1 of the first D/A converter 41 so that the "−Iz" when the switch SW8 is turned on, and the "+Iz" when the switch SW7 is turned on become the same current value. That is, "−Iz" and "+Iz" are constant currents identical in absolute value and opposite in direction to each other, and in the following description, an absolute value (current value) of "−Iz" and "+Iz" is called "supply current value Iz".

As indicated in the third row of FIG. 13, the inter-sensor voltage Vs (voltage between both ends of the electromotive force cell 25) changes with the supply of "−Iz" and "+Iz" to the electromotive force cell 25. In FIG. 13, because the inter-sensor voltage Vs is represented as the voltage of the terminal 23 based on the voltage of the terminal 22, the inter-sensor voltage Vs decreases by the supply of "−Iz" (turning on the switch SW8), and increases by the supply of "+Iz" (turning on the switch SW7).

As indicated by the third row of FIG. 13, the microcomputer 33 detects a pre-current-supply voltage Va which is the inter-sensor voltage Vs immediately before the "−Iz" is supplied to the electromotive force cell 25 (that is, immediately before the switch SW8 is turned on), and a post-current-supply voltage Vb which is the inter-sensor voltage Vs in a period when the "−Iz" is supplied (in this case, immediately before the switch SW8 is turned off).

Further, the microcomputer 33 calculates the impedance Z of the electromotive force cell 25 on the basis of a difference ΔVs (absolute value of a difference between Va and Vb) between the pre-current-supply voltage Va and the post-current-supply voltage Vb, and the supply current value Iz. Specifically, the microcomputer 33 divides the difference ΔVs by the supply current value Iz to calculate the impedance Z (=ΔVs/Iz).

Because the impedance Z of the electromotive force cell 25 has a correlation with the temperature of the electromotive force cell 25, the microcomputer 33 determines whether the electromotive force cell 25 and the oxygen pump cell 26 are in an active state, or not, or controls a heater (not shown) for heating the electromotive force cell 25 and the oxygen pump cell 26, on the basis of the calculated impedance Z.

The reason that after "−Iz" for detecting the impedance Z is supplied to the electromotive force cell 25, "+Iz" opposite to "−Iz" is supplied thereto is to reduce a normal recovery time until a state of the electromotive force cell 25 returns to a normal state for detection of the air-fuel ratio (that is, a state in which the sensor current becomes a value corresponding to the air-fuel ratio). Also, "−Iz" and "+Iz" are supplied to the electromotive force cell 25 in the order opposite to that described above, and "+Iz" may be set to a current for impedance detection. Also, for example, only one of "−Iz" and "+Iz" may be supplied to the electromotive force cell 25.

According to the ECU 10 described above, because the mode of the control circuit 31 can switch over to the one-cell mode and the two-cell mode by the microcomputer 33, the control circuit 31 can be shared by the one-cell air-fuel ratio sensor 1 and the two-cell air-fuel ratio sensor 2.

Also, the connection terminals J1 and J2 used in common for connecting at least the respective air-fuel ratio sensors 1 and 2 of the connection terminals J1 to J3 become in a high impedance state at the time of powering on the ECU 10. After the microcomputer 33 starts by powering on the ECU 10, the microcomputer 33 sets the mode of the control circuit 31 to one of the one-cell mode and the two-cell mode. For that reason, an unnecessary voltage can be surely prevented from being output to the air-fuel ratio sensors 1 and 2 connected to the ECU 10. The high impedance states of the connection terminals J1 and J2 are released by turning on the switches SW10 and SW11.

Also, the control circuit 31 switches over to the one-cell mode or the two-cell mode, depending on which of the switches SW1 and SW2 is turned on, and the operational amplifier 44 can perform different operation between the one-cell mode and the two-cell mode. Hence, a reduction in the scale of the circuit can be realized.

In the above embodiment, because the first D/A converter 41 is used for three functions of controlling the voltage to be applied to the terminal 11 of the one-cell air-fuel ratio sensor 1, controlling "−Iz" and "+Iz", and controlling the label resistance measurement current, the resistors 45, 46, and the switches SW4 to SW6 are provided. For that reason, when those respective controls are implemented by the individual D/A converters, the resistors 45, 46, and the switches SW4 to SW6 become unnecessary. For example, in a configuration where the output voltage Vo1 of the first D/A converter 41 is input to only the non-inverting input terminal of the operational amplifier 44, the output voltage Vo1 of the first D/A converter 41 may be controlled to match the above voltage Vc in the two-cell mode. In this case, the first D/A converter 41 functions as a first voltage variable unit. Also, when the individual D/A converters are provided for controlling the label resistance measurement current, an operational amplifier for controlling the transistor 63 may be provided in addition to the operational amplifier 60. On the other hand, when there is no need to put the connection terminals J1 to J4 into the high impedance state, the switches SW9 to SW12 can be omitted.

Also, the ECU 10 includes the connection terminal J4 connected to one terminals 14 and 24 of the label resistor 17, the circuit (41, 56, 60, 63, SW6, SW9) that supplies the label resistance measurement current to the connection terminal J4, and the switch SW3 for resistance measurement which connects the connection terminal (J1 in the above example) connected with the other end of the label resistor 17, of the connection terminals J1 to J3 to the ground line. The microcomputer 33 turns on the switch SW3, outputs the label resistance measurement current to the above circuit (41, 56, 60, 63, SW6, SW9), and measures the resistance value of the label resistor 17 on the basis of the voltage of the connection terminal J1.

For that reason, even in the one-cell air-fuel ratio sensor 1*a* of the type in which a side of the label resistor 17 opposite to the terminal 14 side is connected to the terminal 11, or the two-cell air-fuel ratio sensor 2*a* of the type in which the side of the label resistor 17 opposite to the terminal 24 side is connected to the terminal 21, the resistance value of the label resistor 17 can be measured. This is because the side of the label resistor 17 opposite to the terminals 14 and 24 side can be connected to the ground line by the switch SW3.

Also, when the one-cell air-fuel ratio sensors 1*a* and 1*b*, or the two-cell air-fuel ratio sensors 2*a* and 2*b* each having the label resistor 17 are connected to the ECU 10, when the microcomputer 33 starts, the microcomputer 33 first performs operation for measuring the resistance value of the label resistor 17, and thereafter sets the mode of the control circuit 31 to one of the one-cell mode and the two-cell mode (refer to FIG. 3). For that reason, after the amount of correction for correcting the characteristic variations of the air-fuel ratio sensors 1*a*, 1*b*, 2*a*, and 2*b* is determined on the basis of the resistance value of the label resistor 17, a process for detecting the air-fuel ratio can be implemented.

The switch SW3 may be provided in any connection terminal of the connection terminals J1 to J3, which is likely to be connected with the end of the label resistor 17. For example, in the one-cell air-fuel ratio sensor 1*a*, the side of the label resistor 17 opposite to the terminal 14 side is connected to the terminal 11 as described above. On the other hand, in the two-cell air-fuel ratio sensor 2*a*, the side of the label resistor 17 opposite to the terminal 24 side is connected to the terminal 22 or the terminal 23. In this case, a switch having the same function as that of the switch SW3 may be provided also in the connection terminal J2 or the connection terminal J3.

The embodiments of the invention have been described above. However, the invention is not limited to the above embodiments, but can be variously embodied. The above-mentioned numeric values are exemplary, and may be other values.

For example, an IC may be used in place of the microcomputer 33.

In addition, a function of one constituent element in the above-described embodiments may be distributed to a plurality of constituent elements, or functions of a plurality of constituent elements may be integrated into one constituent element. In addition, at least a part of the configurations of the above-described embodiments may be substituted with a known configuration having the same function. In addition, a part of the configurations of the above-described embodiments may be omitted as long as the problem can be solved. In addition, all aspects that are included in the technical spirit that is specified in the attached claims are embodiments of the invention.

Also, the invention can be realized by various configurations such as a system having the ECU as a component, a program for causing a computer to function as the ECU, a medium storing the program therein, or a method for controlling the air-fuel ratio sensor, in addition to the above-mentioned ECU.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. An air-fuel ratio sensor control device that is connected with one of: a two-cell type air-fuel ratio sensor having an electromotive force cell and an oxygen pump cell, which are oxygen concentration cells in such a manner that a pump current flowing in the oxygen pump cell is controlled so that an output voltage of the electromotive force cell reaches a target value, and the pump current becomes a current corresponding to an air-fuel ratio; and a one-cell type air-fuel ratio sensor having a single cell, in which a current corresponding to the air-fuel ratio flows under a state where a voltage is applied to the single cell, wherein the two-cell type air-fuel ratio sensor includes: a first two-cell terminal that is connected to one electrode in a pair of electrodes in the oxygen pump cell; a second two-cell terminal that is connected to both of another electrode in the pair of electrodes in the oxygen pump cell and one electrode in a pair of electrodes in the electromotive force cell; and a third two-cell terminal that is connected to another electrode in the pair of electrodes in the electromotive force cell, as terminals for controlling the two-cell type air-fuel ratio sensor, and wherein the one-cell type air-fuel ratio sensor includes: a first one-cell terminal that is connected to one electrode in a pair of electrodes in the single cell; and a second one-cell terminal that is connected to another electrode in the pair of electrodes in the single cell, as terminals for controlling the one-cell type air-fuel ratio sensor, the air-fuel ratio sensor control device comprising:

a first connection terminal, a second connection terminal, and a third connection terminal, as terminals for connecting one of the two-cell type air-fuel ratio sensor and the one-cell type air-fuel ratio sensor;

a control circuit that is switchable, by turning on and off at least one changeover switch, between a one-cell circuit configuration and a two-cell circuit configuration, the two-cell circuit configuration controlling the two-cell type air-fuel ratio sensor through the first, second, and third connection terminals, and the one-cell circuit configuration controlling the one-cell type air-fuel ratio sensor through the first and second connection terminals; and a control unit that sets a circuit configuration of the control circuit to one of the one-cell circuit configuration and the two-cell circuit configuration, by controlling the at least one changeover switch, wherein, when the air-fuel ratio sensor control device is connected with the two-cell type air-fuel ratio sensor, the first connection terminal is connected with the first two-cell terminal, the second connection terminal is connected with the second two-cell terminal, and the third connection terminal is connected with the third two-cell terminal, wherein, when the air-fuel ratio sensor control device is connected with the one-cell type air-fuel ratio sensor, the first connection terminal is connected with the first one-cell terminal, and the second connection terminal is connected with the second one-cell terminal, wherein the control circuit includes:

a first voltage variable unit that has an output voltage varied according to an instruction from the control unit;

a second voltage variable unit that has an output voltage varied according to the instruction from the control unit;

an operational amplifier having a non-inverting input terminal, to which the output voltage of the first voltage variable unit is input, and an output terminal connected to the first connection terminal;

a first switch that connects an inverting input terminal and the output terminal of the operational amplifier when the first switch turns on;

a second switch that connects the inverting input terminal of the operational amplifier and the second connection terminal when the second switch turns on;

a current detection resistor that has one end, to which the output voltage of the second voltage variable unit is applied, and the other end connected to the second connection terminal;

a first voltage output unit that inputs a voltage corresponding to a voltage difference between both ends of the current detection resistor into the control unit;

a second voltage output unit that inputs a voltage corresponding to a voltage difference between the second connection terminal and the third connection terminal into the control unit;

a first current supply unit that supplies a constant current for functioning the electromotive force cell to the third connection terminal; and a second current supply unit that supplies a constant current for measuring an impedance of the electromotive force cell to the third connection terminal, wherein the first and second switches function as the changeover switch, wherein the control circuit is in the one-cell circuit configuration when the control unit turns on the first switch, and wherein the control circuit is in the two-cell circuit configuration when the control unit turns on the second switch.

2. The air-fuel ratio sensor control device according to claim 1, wherein at least the first and second connection terminals utilized in common for connecting the one of the two-cell type air-fuel ratio sensor and the one-cell type air-fuel ratio sensor are in a high impedance state when starting to energize the air-fuel ratio sensor control device, and wherein the control unit cancels the high impedance state of the first and second connection terminals after starting to energize the air-fuel ratio sensor control device, and sets the circuit configuration of the control circuit to the one of the one-cell circuit configuration and the two-cell circuit configuration.

3. An air-fuel ratio sensor control device that is connected with one of: a two-cell type air-fuel ratio sensor having an electromotive force cell and an oxygen pump cell, which are oxygen concentration cells in such a manner that a pump current flowing in the oxygen pump cell is controlled so that an output voltage of the electromotive force cell reaches a target value, and the pump current becomes a current corresponding to an air-fuel ratio; and a one-cell type air-fuel ratio sensor having a single cell, in which a current corresponding to the air-fuel ratio flows under a state where a voltage is applied to the single cell, wherein the two-cell type air-fuel ratio sensor includes: a first two-cell terminal that is connected to one electrode in a pair of electrodes in the oxygen pump cell; a second two-cell terminal that is connected to both of another electrode in the pair of electrodes in the oxygen pump cell and one electrode in a pair of electrodes in the electromotive force cell; and a third two-cell terminal that is connected to another electrode in the pair of electrodes in the electromotive force cell, as terminals for controlling the two-cell type air-fuel ratio sensor, and wherein the one-cell type air-fuel ratio sensor includes: a first one-cell terminal that is connected to one electrode in a pair of electrodes in the single cell; and a second one-cell terminal that is connected to another electrode in the pair of electrodes in the single cell, as terminals for controlling the one-cell type air-fuel ratio sensor, the air-fuel ratio sensor control device comprising:

a first connection terminal, a second connection terminal, and a third connection terminal, as terminals for connecting one of the two-cell type air-fuel ratio sensor and the one-cell type air-fuel ratio sensor;

a control circuit that is switchable, by turning on and off at least one changeover switch, between a one-cell circuit configuration and a two-cell circuit configuration, the two-cell circuit configuration controlling the two-cell type air-fuel ratio sensor through the first, second, and third connection terminals, and the one-cell circuit configuration controlling the one-cell type air-fuel ratio sensor through the first and second connection terminals; and a control unit that sets a circuit configuration of the control circuit to one of the one-cell circuit configuration and the two-cell circuit configuration, by controlling the at least one changeover switch, wherein at least one of the one-cell type air-fuel ratio sensor and the two-cell type air-fuel ratio sensor includes: a label resistor having a resistance measured for correcting a characteristic variation of the air-fuel ratio sensor; and a resistor terminal that is connected to one end of the label resistor, wherein, in the at least one of the one-cell type air-fuel ratio sensor and the two-cell type air-fuel ratio sensor, the other end of the label resistor is connected to one of the first one-cell terminal, the second one-cell terminal, the first two-cell terminal, the second two-cell terminal and the third two-cell terminal, the air-fuel ratio sensor control device further comprising:

a fourth connection terminal that is connected to the resistor terminal;

a resistance measurement current supply unit that supplies a current, for measuring a resistance of the label resistor, to the fourth connection terminal according to an instruction from the control unit; and a resistance measurement switch that connects one of the first, second, and third connection terminals, which is connected with the other end of the label resistor, to a ground line when the resistance measurement switch turns on, wherein the control unit turns on the resistance measurement switch, wherein the control unit outputs a current, for measuring the resistance of the label resistor, to the resistance measurement current supply unit, and wherein the control unit measures the resistance of the label resistor based on a voltage of the fourth connection terminal.

4. The air-fuel ratio sensor control device according to claim 3, wherein the control unit performs an operation for measuring the resistance of the label resistor when starting to energize the air-fuel ratio sensor control device, and wherein the control unit sets the circuit configuration of the control circuit to one of the one-cell circuit configuration and the two-cell circuit configuration after the control unit performs the operation for measuring the resistance of the label resistor.

\* \* \* \* \*